(12) United States Patent
Gowrishankar et al.

(10) Patent No.: US 7,176,028 B2
(45) Date of Patent: Feb. 13, 2007

(54) METHOD OF ALTERING LEVELS OF PLASMIDS

(75) Inventors: Jayaraman Gowrishankar, Hyderabad (IN); Rajendran Harinarayanan, Hyderabad (IN)

(73) Assignee: Centre for DNA Fingerprinting and Diagnostics (CDFD), Hyderabad (IN)

( * ) Notice: Subject to any disclaimer, the term of this patent is extended or adjusted under 35 U.S.C. 154(b) by 624 days.

(21) Appl. No.: 10/266,510

(22) Filed: Oct. 8, 2002

(65) Prior Publication Data

US 2004/0067589 A1 Apr. 8, 2004

(51) Int. Cl.
C12N 15/74 (2006.01)

(52) U.S. Cl. ...................................... 435/471
(58) Field of Classification Search ................ 435/471, 435/440
See application file for complete search history.

(56) References Cited

OTHER PUBLICATIONS

Zellars et al. Antiterminator-dependent modulation of transcription elongation rates by NusB and NusG. Molecular Microbiology (1999), vol. 32 (6), pp. 1296-1304.*
Steiner et al. Crystal structures of transcription factor NusG in light of its nucleic acid- and prpotein-niding activities. The EMBO Journal (2002) vol. 21 (17), pp. 4641-4653.*
Rudd KE (1998) "Linkage Map of *Escherichia coli* K-12, Edition 10: The Physical Map", *Microbiol. Mol. Biol. Rev.* 62(3):985-1019.
Blattner FR et al. (1997) "The Complete Genome Sequence of *Escherichia coli* K-12", *Science* 277:1453-1462.
Martinez A et al. (1996) "Mutational Analysis and Secondary Structure Model of the RNP1-like Sequence Motif of Transcription Termination Factor Rho", *J. Mol. Biol.* 257:895-908.
Marians KJ (1996) "Replication Fork Progression", in *Escherichia coli* and *Salmonella*: Cellular and Molecular Biology, 2nd edition, vol. I (Neidhart et al., eds), *ASM Press*, Washington D.C., USA, Chapter 50, pp. 749-763.
Lin-Chao S et al. (1992) "High copy number of the pUC plasmid results from a Rom/Rop-suppressible point mutation in RNA II", *Mol. Microbiol.* 6(22):3385-3393.
Nordstrom K et al. (1992) "Runaway-Replication Plasmids As Tools to Produce Large Quantities of Proteins from Cloned Genes in Bacteria", *Bio/Technology* 10:661-666.
Sullivan SL et al. (1992) "Requirement for *E. coli* NusG Protein in Factor-Dependent Transcription Termination", *Cell* 68:989-994.

Gil D et al. (1991) "ColE1-type vectors with fully repressible replication" *Gene* 105:17-22.
Lerner CG et al. (1990) "Low copy number plasmids for regulated low-level expression of cloned genes in *Escherichia coli* with blue/white insert screening capability" *Nucleic Acids Res.* 18(15):4631.
Hamilton et al. (1989) J. Bacteriol. 171:4617-4622, "New method for generating deletions and gene replacements in *Escherichia coli*".
Polisky B (1988) "ColE1 Replication Control Circuitry: Sense from Antisense" *Cell* 55:929-932.
Kohara Y et al. (1987) "The Physical Map of the World *E. coli* Chromosome: Application of a New Strategy for Rapid Analysis and Sorting of a Large Genomic Library" *Cell* 50:495-508.
Lopilato J et al. (1986) "Mutations in a new chromosomal gene of *Escherichia coli* K-12, pcnB, reduce plasmid copy number of pBR322 and its derivatives" *Mol. Gen. Genet.* 205:285-290.
Yanisch-Perron et al. (1985) "Improved M13 phage cloning vectors and host strains: nucleotide sequences of the M13mp18 and pUC19 vectors" *Gene* 33:103-119.
Covarrubias L et al. (1982) "Construction and characterization of new cloning vehicles VI. Plasmid pBR329, a new derivative of pBR328 lacking the 482 base-pair inverted duplication" *Gene* 17:79-89.
Chang AC et al. (1978) "Construction and Characterization of Amplifiable Multicopy DNA Cloning Vehicles Derived from the P15A Cryptic Miniplasmid" *J. Bacteriol.* 134(3):1141-1156.
Susan L. Sulivan and Max E. Gottesman: Requirement For *E.coli* NusG Protein in Factor-Dependent Transcription Termination; Cell, vol. 68, 989-994, Mar. 6, 2002.
Joyce Li et al., Elongation factor NusG interacts with termination factor p to regulate termination and anti-termination of transcription, Genes and Development 7:161-172.
John P. Richardson et al., Control of RNA Chain Elongation and Termination; pp. 822-848.
Evgency Nudler et al., Transcription Termination and anti-termination in *E. coli*, Genes to Cells (2002) 7, 755-768.
D.E. Morse et al., Amber *suA* Mutations which Relieve Polarity; J. Mol. Biol. (1972) 63, 605-608.
Evidence That Mutations in the suA Polarity Suppressing Gene Directly Affect Termination Factor rho; Nature vol. 259, Jan. 15, 1976; 151-153.

(Continued)

*Primary Examiner*—Remy Yucel
*Assistant Examiner*—Tara L. Garvey
(74) *Attorney, Agent, or Firm*—Ann S. Hobbs; VENABLE LLP

(57) ABSTRACT

The present invention relates to a method of obtaining altered plasmid contents in bacteria, bearing mutation in at least one of the chromosomal genes, nusG, rho, and dnaC, and the bacterial strains thereof, having the mutated chromosomal genes, individually or in various possible combinations, capable of altering the level of plasmids.

6 Claims, No Drawings

OTHER PUBLICATIONS

R. Harinarayanan et al., Host Factor Titration by Chromosomal R-loops as a Mechanism for Runway Plasmid Replication of Transcription Termination-defective Mutants of *Escherichia coli*, J. Mol. Bioo. 332, 31-46, (2003).

Annie C.Y. Chang, Construction and Characterization of Amplifiable Multicopy DNA Cloning Vehicles Derived from the P15A Cryptic Miniplamid; Journal of Bacteriology, Jun. 1978, p. 1141-1156.

Robert E. Bird; Homology Between *Escherichia coli* Plasmids ColE1 and p15A; Journal of Bacteriology, vol. 145, No. 3, Mar. 1981; p. 1305-1309.

Gerald Selzer et al., Specific Cleavage of the p15A Primer Precursor by Ribonuclease H at the Origin of DNA Replication, Proc. Natl. Acad. Sci. USA, vol. 79, pp. 7082-7086, Dec. 1982.

Gerald Selzer et al., The Origin of Replication of Plasmid p15A and Comparative Studies on the Nucleotide Sequences Around the Origin of related Plasmids; Cell. vol. 32, 119-129, Jan. 1983.

Michael G. Jobling et al., Construction of Vectors with the p15a Replicon, Kanamycin Resistance, Inducible *IacZα* and pUC18 or pUC19 Multiple Cloning Sites; Nucleic Acids Research, vol. 18, No. 17, 5315-5316 (1990).

Luz-Maria Guzman et al., Tight Regulation, Modulation, and High-Level Expression by Vectors Containing the Aravinose PBAD Promoter; vol. 177, No. 14; Journal of Bacteriology, Jul. 1995, p. 4121-4130.

\* cited by examiner

METHOD OF ALTERING LEVELS OF PLASMIDS

The present invention relates to process for plasmid DNA that enables either an increased plasmid content in host bacterial cells and increased yield of plasmid DNA, or a decreased plasmid content in host bacterial cells.

BACKGROUND OF THE INVENTION

Plasmids are stable extra-chromosomal genetic elements in bacteria that are most commonly comprised of circular DNA (often a few kilobase-pairs [kb] in size) and that are capable of autonomous replication within bacterial cells. With the advent of recombinant DNA technology, plasmids gained use in a variety of processes as vehicles or vectors for the introduction and maintenance of non-native DNA in bacterial host cells. More recently, plasmids have become important as products as well, in the form of DNA vaccines in medical and veterinary practice. In most such applications, the bacterial host is *Escherichia coli*.

An important feature in relation to plasmids is their copy-number regulation within bacterial cells. Under ordinary growth conditions, each plasmid is maintained at a characteristic copy number in the cell by the operation of feedback regulatory loops that control replication of the plasmid DNA. One class of plasmids which is extensively employed in biotechnology are the "ColE1-like" plasmids which include the naturally occurring plasmids ColE1, p15A, RSF1030, CloDF13, and pMB1 as well as the cloning vectors pBR322, pBR329, pACYC184, pACYC177 and the pUC and pBluescript series of plasmids. In the replication of the ColE1-like plasmids in *E. coli*, the feedback regulatory loops involve a plasmid-specific RNA species (RNA-II) that activates replication, and a second plasmid-specific RNA species (RNA-I) and a protein (Rop) that act to inhibit replication [Polisky (1988) Cell 55:929–932].

Alterations in copy numbers of plasmids—both upward and downward—have been sought to be achieved by manipulation of the concerned feedback regulatory loops in the prior art, as briefly described below. Manipulations to increase the plasmid copy number are in general desirable when one's aim is (i) to increase the yields of plasmid DNA from cultures, for example, in routine recombinant DNA experiments or in production of DNA vaccines; or (ii) to increase the expression of product(s) encoded by plasmid-borne gene(s). Increase in plasmid copy numbers have been achieved either constitutively by mutations inactivating the feedback regulatory circuits (present, for example, in the commonly used ColE1-derived pUC series of plasmid vectors with very high copy numbers, such as pUC18 or pUC19) or by inducible processes that have been referred to as runaway-plasmid-replication systems [Lin-Chao et al. (1992) Mol. Microbiol. 6:3385–3393; Nordstrom and Uhlin (1992) Bio/Technology 10:661–666].

Manipulations to decrease the plasmid copy number become valuable in situations where the gene(s) borne on the plasmid confer a dosage-dependent growth disadvantage to the host bacterial cells. Mutation in pcnB, an *E. coli* chromosomal gene, has been shown to reduce the copy number of both ColE1-derived and p15A-derived plasmids, most probably through stabilization of the RNA-I transcripts involved in the negative control of plasmid replication [Lopilato et al. (1986) Mol. Gen. Genet. 205:285–290].

OBJECTS OF THE PRESENT INVENTION

The main object of the present invention is to develop a method of obtaining altered plasmid content in bacterium bearing mutation in at least one of the chromosomal genes nusG, rho, and dnaC.

Another main object of the present invention is to develop a method wherein the gene nusG mutation leads to an increase in the level of the plasmids.

Yet another object of the present invention is to develop a method wherein the gene rho mutation leads to an increase in the level of the plasmids.

Still another object of the present invention is to develop a method wherein the gene dnaC mutation leads to decrease in the level of the plasmids.

Still another object of the present invention is to develop a method of alteration of level of plasmids wherein the difference in the level of the plasmids is about 10 folds.

Still another object of the present invention is to develop an *E.Coli* strain having genotype of MC4100 nusG argE86::Tn10 dnaC zjj901::Tn10dKan.

Still another main object of the present invention is to develop an *E.Coli* strain having mutation in codon 146 of the nusG gene resulting in a Glycine-to-aspartate substitution at the cognate amino acid position of the encoded protein.

Still another object of the present invention is to develop an *E.Coli* strain having mutation in codon 243 of the rho gene resulting in a alanine-to-glutamate substitution at the cognate amino acid position of the encoded protein.

Still another object of the present invention is to develop an *E.Coli* strain having mutation in codon 84 of the dnaC gene resulting in a alanine-to- threonine substitution at the cognate amino acid position of the encoded protein.

Still another object of the present invention is to develop an *E.coli* strain, transformed with conditional replicon plasmids pHYD751, pHYD763, and pHYD1201, individually or in various possible combinations.

Still another object of the present invention is to develop plasmid pHYD751 as IPTG (isopropyl beta-D-thiogalacto-pyranoside)-dependent conditional replicon of gene nusG.

Still another object of the present invention is to develop a plasmid pHYD763 as temperature-sensitive conditional replicon of gene nusG.

Still another object of the present invention is to develop a plasmid pHYD1201 as temperature-sensitive conditional replicon of gene rho.

SUMMARY OF THE INVENTION

The present invention relates to a method of obtaining altered plasmid content in bacteria bearing mutation in at least one of the chromosomal genes, nusG, rho, and dnaC, and the bacterial strains thereof, having the mutated chromosomal genes, individually or in various possible combinations, capable of altering the level of plasmids.

DETAILED DESCRIPTION OF THE PRESENT INVENTION

Accordingly, the present invention relates to a method of obtaining altered plasmid contents in bacteria, bearing mutation in at least one of the chromosomal genes, nusG, rho, and dnaC, and the bacterial strains thereof, having the mutated chromosomal genes, individually or in various possible combinations, capable of altering the level of plasmids.

In an embodiment of the present invention, a method of obtaining altered plasmid content in bacterium bearing mutation in at least one of the chromosomal genes nusG, rho, and dnaC, said method comprising steps of:

(a) introducing mutation in the said chromosomal gene(s) of the host bacterium, (b) maintaining a functional copy of the said chromosomal gene(s) on a conditional replica in the said bacterium, (c) culturing the said bacterium under conditions permissive for intra-cellular replication and maintenance of conditional replica, (d) shifting the bacterium to a restrictive conditions that does not permit further intra-cellular replication of the conditional replica, (e) estimating the level of the plasmid vectors in the bacterium in both permissive and restrictive conditions, and (f) calculating the difference in the level of the plasmid vectors in the bacterium in both permissive and restrictive conditions in the said gene(s).

In another embodiment of the present invention, wherein the gene nusG shows GC-to-AT transition mutation at codon 146, resulting in a glycine-to-aspartate substitution at the cognate amino acid.

In yet another embodiment of the present invention, wherein the gene rho shows GC-to-TA transition mutation at codon 243, resulting in alanine-to-glutamate substitution at the cognate amino acid.

In still another embodiment of the present invention, wherein the gene dnaC shows GC-to-AT transition mutation at codon 83, resulting in alanine-to-threonine substitution at the cognate amino acid.

In still another embodiment of the present invention, wherein the bacteria of family Enterobacteriaceae are host bacteria.

In still another embodiment of the present invention, wherein host bacteria are preferably *E.Coli*.

In still another embodiment of the present invention, wherein the plasmid vectors are preferably from a group comprising ColE1-derived plasmids, and p15A-derived plasmids.

In still another embodiment of the present invention, wherein the ColE1-derived plasmids are members of incompatibility group, comprising plasmids pBR322, pBR329, pUC series of plasmids, pBluescript series of plasmids and their derivatives.

In still another embodiment of the present invention, wherein the p15A-derived plasmids are members of the p15A incompatibility group, comprising plasmids pACYC184 and pACYC177, and their derivatives.

In still another embodiment of the present invention, wherein the gene nusG mutation leads to an increase in the level of the plasmids.

In still another embodiment of the present invention, wherein the gene rho mutation leads to an increase in the level of the plasmids.

In still another embodiment of the present invention, wherein the gene dnaC mutation leads to decrease in the level of the plasmids.

In still another embodiment of the present invention, wherein the difference in the level of the plasmids is about 10 fold.

In still another embodiment of the present invention, wherein conditional replica is selected from a group comprising plasmids pHYD751, pHYD763, and pHYD1201.

In still another embodiment of the present invention, wherein conditional replica shows non-mutated gene(s) comprising nusG, rho, and dnaC, individually or in various possible combinations.

In still another embodiment of the present invention, wherein said method helps obtain genes of interest at desired levels.

In still another embodiment of the present invention, wherein an *E. Coli* strain of genotype MC4100 nusG argE86::Tn10dnaC zjj901::Tn10dKan of accession No. NCIMB 41132, deposited at NCIMB Limited, Scotland, U.K.

In still another embodiment of the present invention, wherein said strain carries a GC-to-AT transition mutation in codon 146 of the chromosomal nusG gene, resulting in a Glycine-to-aspartate substitution at the cognate amino acid position of the encoded protein, along with an argE86::Tn10 mutation approximately 25% linked to nusG in phage P1 transduction.

In still another embodiment of the present invention, wherein said strain carries a GC-to-AT transition mutation in codon 84 of the chromosomal dnaC gene, resulting in a alanine-to-threonine substitution at the cognate amino acid position of the encoded protein, along with an zjj-901::Tn10dKan insertion approximately 88% linked to dnaC in phage P1 transduction.

In still another embodiment of the present invention, wherein a plasmid pHYD751.

In still another embodiment of the present invention, wherein said plasmid is an IPTG (isopropyl beta-D-thiogalactopyranoside)-dependent conditional replicon of gene nusG.

In still another embodiment of the present invention, wherein a plasmid pHYD763.

In still another embodiment of the present invention, wherein said plasmid is a temperature-sensitive conditional replicon of gene nusG.

In still another embodiment of the present invention, wherein a plasmid pHYD1201.

In still another embodiment of the present invention, wherein said plasmid is a temperature-sensitive conditional replicon of gene rho.

In another embodiment of the present invention, wherein notwithstanding the above-mentioned prior art developments, there continues to exist a need for additional and improved procedures to increase or to decrease plasmid DNA copy numbers and yields, given the extensive applications of plasmid-based recombinant DNA technology as also the yield demands imposed by the use of plasmids as DNA vaccines.

In another embodiment of the present invention, wherein novel processes that we have developed for alterations of plasmid DNA content in and yield from host bacterial cells, by the employment of strains bearing a mutation in at least one of the following genes nusG, rho, or dnaC. Preferably the bacterial cells are of bacteria of the family Enterobacteriaceae, e.g., *Escherichia coli*. The nusG and rho gene products have been implicated in transcription termination and/or antitermination reactions within the bacterial cell [Sullivan et al. (1992) Cell 68:989–994; Martinez et al. (1996) J. Mol. Biol. 257:895–908], while the dnaC gene product participates in chromosomal and plasmid DNA replication in vivo [Marians (1996) "Replication Fork Progression", in *Escherichia coli* and *Salmonella*: Cellular and Molecular Biology, 2$^{nd}$ edition" (Neidhardt et al., eds), ASM Press, Washington D.C., USA, Chapter 50, pp. 749–763]. There has been no description in the prior art of processes employing mutations in any of these genes for alterations of plasmid DNA content in and yield from the cognate host bacterial cells.

In another embodiment of the present invention, wherein one aspect of the invention features a method of increasing the copy number of plasmids in host bacterial cells with mutation in the nusG gene.

In another embodiment of the present invention, wherein the invention provides a method for increasing the copy number of plasmids wherein (i) the host bacterial cells carries a mutation in the chromosomal nusG gene, (ii) the said cells also carry a functional nusG+ gene on a conditional replicon, (iii) the bacterium is cultured under conditions permissive for intracellular replication and maintenance of the conditional replicon, and (iv) the culture is subsequently shifted to a restrictive condition that does not permit further replication of the conditional replicon.

In another embodiment of the present invention, wherein a method for increasing the copy number of plasmids in host bacterial cells with mutation in the rho gene.

In another embodiment of the present invention, wherein a method for increasing the copy number of plasmids wherein (i) the host bacterial cells carry a mutation in the chromosomal rho gene, (ii) the said cells also carry a functional rho+ gene on a conditional replicon, (iii) the bacterium is cultured under conditions permissive for intracellular replication and maintenance of the conditional replicon, and (iv) the culture is subsequently shifted to a restrictive condition that does not permit further replication of the conditional replicon.

In another embodiment of the present invention, wherein a method for decreasing the plasmid copy number in and yield from host bacterial cells with mutation in the dnaC gene.

In another embodiment of the present invention, wherein a preferred aspect of the invention is its applicability to ColE1-derived plasmids and p15A-derived plasmids.

In another embodiment of the present invention, wherein as used herein, "ColE1-derived plasmid" is a plasmid that is a member of the ColE1 incompatibility group, and includes, for example, the plasmids pBR322, pBR329, pUC series of plasmids, and pBluescript series of plasmids and their derivatives.

In another embodiment of the present invention, wherein as used herein, "p15A-derived plasmid" is a plasmid that is a member of the p15A incompatibility group, and includes, for example, the plasmids pACYC184 and pACYC177 and their derivatives.

In another embodiment of the present invention, wherein as used herein, "conditional replicon" is an extra-chromosomal genetic element capable of autonomous replication within a host bacterial cell under certain conditions of growth of the bacterial culture that are said to be "permissive" but not under certain other culture conditions that are said to be "restrictive".

In another embodiment of the present invention, wherein unless otherwise defined, all technical and scientific terms used herein have the same meaning as commonly understood by one of ordinary skill in the art to which this invention belongs. In case of conflict, the present application, including definitions, will control. All publications, patents, and other references mentioned herein are incorporated by reference.

In compliance with the requirements of full disclosure, the following strain of this invention has been deposited in the NCIMB Ltd., 23 St Machar Drive, Aberdeen AB24 3RY, Scotland, United Kingdom, under the Budapest Treaty Rules, prior to the filing date of this application. The deposit made is of the *Escherichia coli* strain GJ3158, under the accession number NCIMB 41132 dated May 24, 2002.

Strain GJ3158 was constructed from strain MC4100 in several steps of phage P1-mediated transduction. The genotype of strain GJ3158 is described below.

In another embodiment of the present invention, wherein the widespread employment of plasmids in a variety of recombinant DNA processes has created the need for additional new and improved methods to manipulate, both upward and downward, the copy number of such plasmids in host bacterial cells. Methods to increase plasmid DNA content are also particularly useful in the context of industrial production of DNA vaccines. Accordingly, the present invention provides several methods for increasing and decreasing plasmid DNA content in host bacterial cells. These methods are based on discoveries of certain novel properties of bacterial cells with mutations in the nusG, rho, or dnaC genes, herein described.

In another embodiment of the present invention, wherein in the art, *Escherichia coli* is the preferred host bacterium for various recombinant DNA processes; and ColE1-derived plasmids and p15A-derived plasmids are amongst the preferred plasmid vectors employed in these processes. In the production of DNA vaccines, ColE1-derived plasmids with certain mutations (in the replication primer RNA-II) and/or deletions (of the gene encoding a small protein designated Rop or Rom) that lead to increased plasmid copy numbers in the host bacterial cells, are preferred e.g., derivatives of the pUC or pBluescript series of plasmids.

In another embodiment of the present invention, wherein the use of *E. coli* as host bacterium is also a preferred aspect of the present invention. Likewise, the use of ColE1-derived plasmids and p15-A derived plasmids is another preferred aspect of the present invention. A further preferred aspect of the invention is the use of very high-copy-number ColE1-derived plasmids with mutation in RNA-II and/or deletion of Rom, e.g., pUC or pBluescript series of plasmids.

In another embodiment of the present invention, wherein according to one aspect of the invention, the nusG mutation is one, which reduces the function of the encoded protein. Example 1 below describes this aspect of the invention with respect to the employment of an *E. coli* host bacterium with a GC-to-AT transition mutation in codon 146 of the chromosomal nusG gene resulting in a glycine-to-aspartate substitution at the cognate amino acid position of the encoded protein, in combination with the p15A-derived plasmid pACYC184 within the said host bacterial cell. It may be noted that the same alteration in the nusG-encoded protein may be obtained by any of a variety of methods known to the art, and that other mutations in nusG, or plasmid derivatives other than pACYC184, may be employed by a skilled artisan with expectations of similar results.

In another embodiment of the present invention, wherein according to another aspect of the invention, the host bacterial cell bearing a chromosomal nusG mutation also carries a conditional replicon with a functional nusG+ gene. The comprised steps in the method include one in which the bacterium is initially cultured under conditions permissive for intracellular replication and maintenance of the conditional replicon, followed by one wherein the culture is subsequently incubated at a restrictive condition that does not permit further replication of the conditional replicon. Example 2 below describes the construction of plasmid pHYD763, a temperature-sensitive conditional replicon with nusG+, and its employment in a host bacterial cell with a GC-to-AT transition mutation in codon 146 of the chromosomal nusG gene resulting in a glycine-to-aspartate substitution at the cognate amino acid position of the encoded protein, to manipulate plasmid content of the p15A-derived plasmid pACYC184. Example 3 below describes the construction of plasmid pHYD751, a conditional replicon with nusG+ whose replication is dependent on the presence of isopropyl beta-D-thiogalactopyranoside (IPTG) in the culture medium, and its employment in a host bacterial cell with a GC-to-AT transition mutation in codon 146 of the chromosomal nusG gene resulting in a glycine-to-aspartate substitution at the cognate amino acid position of the encoded protein, to manipulate plasmid content of one of the pUC series of plasmids, pUC4K. It may be noted that based on the teachings of the prior art, other chromosomal mutations in nusG including null or knock-out mutations, other methods to construct plasmids equivalent to pHYD763 or pHYD751, other conditional replicons with the nusG+ gene, or plasmids other than pACYC184 or pUC4K, may be alternatively employed by the skilled artisan in the practice of these aspects of the invention.

In another embodiment of the invention, the rho mutation is one which reduces the function of the encoded protein. Example 4 below describes one example of the practice of this aspect of the invention, comprising the use of a rho-4 mutation in an *E. coli* host bacterium in combination with the p15A-derived plasmid pACYC184 within the said host bacterial cell. It may be noted that other mutations in rho, or plasmid derivatives other than pACYC184, may be employed by an ordinarily skilled artisan with expectations of similar results.

In another embodiment of the present invention, wherein according to yet another embodiment of this invention, the host bacterial cell bearing a chromosomal rho mutation also carries a conditional replicon with a functional rho+ gene. The comprised steps in the method include one in which the bacterium is initially cultured under conditions permissive for intracellular replication and maintenance of the conditional replicon, followed by one wherein the culture is subsequently incubated at a restrictive condition that does not permit further replication of the conditional replicon. Example 5 below describes the employment, in a host bacterial cell with a chromosomal rho-4 mutation, of the plasmid pPMrhoCam, a temperature-sensitive conditional replicon with rho+, to manipulate plasmid content of the p15A-derived plasmid pACYC184. Example 6 below describes the construction of plasmid pHYD1201, a conditional replicon with rho+ whose replication is dependent on the presence of IPTG in the culture medium, and its employment in a host bacterial cell with a chromosomal rho-4 mutation, to manipulate plasmid content of one of the pUC series of plasmids, pUC4K. It may be noted that based on the teachings of the prior art, other chromosomal mutations in rho including null or knock-out mutations, other methods to construct plasmids equivalent to pHYD1201, other conditional replicons with rho+, or plasmids other than pACYC184 or pUC4K may be alternatively employed by the skilled artisan in the practice of these aspects of the invention.

In another embodiment of the present invention, wherein a mis-sense mutation in the dnaC gene. Example 7 below describes one example of the practice of this aspect of the invention, comprising the employment of an *E. coli* host bacterium with a GC-to-AT transition mutation in codon 84 of the chromosomal dnaC gene resulting in an alanine-to-threonine substitution at the cognate amino acid position of the encoded protein, in combination with the following plasmids pACYC184, pBR329, or pUC19, within the said host bacterial cell. It may be noted that the same alteration in the dnaC-encoded protein may be obtained by any of a variety of methods known to the art, and that other mutations in dnaC, or plasmid derivatives other than pACYC184, pBR329 or pUC19, may be employed by an ordinarily skilled artisan with expectations of similar results.

In another embodiment of the present invention, wherein the processes described in the present invention can be used to increase the yields of plasmid DNA, to increase the expression of products encoded by plasmid genes, and to reduce the toxicity associated with certain genes at high copy numbers.

In another embodiment of the present invention, wherein the examples given are merely illustrative of the uses, processes and products such as vectors and strains claimed in this invention, and the practice of the invention itself is not restricted to or by the examples described. It is to be expected that additional configurations of the same invention, and/or alternative means by which it is reduced to practice, may be achieved by modifications that involve materials and processes that are already known and well established in the art. It may also be noted in this context that orthologs of the nusG, rho, and dnaC genes have been identified in a variety of Gram-negative and Gram-positive bacteria.

EXAMPLES

The examples further describe and demonstrate embodiments within the scope of the present invention. The examples are given solely for the purpose of illustration and are not to be construed as limitations of the present invention, as many variations thereof are possible without departing from the spirit and scope of the invention.

In the following examples, the following materials and methods were used throughout:

1. The genotypes of *Escherichia coli* strains used in the examples are listed in the Table below.

| Strain | Genotype |
| --- | --- |
| CAG18431 | ilv-500::Tn10 |
| CGSC5072 | leu-277(Am) trpE9851(Oc) IN(rrnD-rrnE)1 rho-4 |
| JBK246 | fhuA2 lacY1 glnV44 hisG1 rpsL9 malT1 xylA7 mtlA2 metB1 rpoB7 rpoB2(Ts) thi-1 |
| MC4100 | delta (argF-lac)U169 rpsL150 relA1 araD139 flbB5301 deoC1 ptsF25 |
| MC4100 recA::Kan | MC4100 recA::Kan |
| GJ862 | same as MC4100 |
| GJ863 | MC4100 rho-4 |
| GJ1504 | MC4100 nusG |
| GJ1514 | JBK246 recA::Kan |
| GJ3140 | MC4100 dnaC zjj-901::Tn10Kan |
| GJ3141 | MC4100 zjj-901::Tn10dKan |
| GJ3158 | MC4100 nusG argE86::Tn10 dnaC zjj-901::Tn10dKan |

Strains CAG18431, CGSC5072, JBK246, and MC4100 are available from the Coli Genetic Stock Center, 830 Kline Biology Tower, MCD Biology Department, 266 Whitney Ave., P.O. Box 20813, Yale University, New Haven, Conn. 06520-8193, USA. Strain MC4100 recA::Kan was obtained from Prof R. Jayaraman, School of Biological Sciences, Madurai Kamaraj University, Madurai 625 014, India. Strain GJ3158 is a strain of this invention that has been deposited under the accession number NCIMB 41132 at the NCIMB Ltd, Scotland. Other strains listed above are described in the examples.

2. Bacteriophage P1 was obtained from Prof. A. J. Pittard, Dept. of Microbiology and Immunology, University of Melbourne, Parkville, Victoria 3052, Australia, and is also available from the NCCB/CBS (The Netherlands Culture Collection of Bacteria), P.O. Box 85167, 3508 AD Utrecht, The Netherlands (http://www.cbs.knaw.nl/Nccb). Bacteriophage lambda clone 556 of the ordered lambda phage library of the *E. coli* genome was obtained from Dr. K. Isono, Dept. of Biology, Faculty of Science, Kobe University, Japan, and is described in Kohara et al. [Cell (1987) 50:495–508]; it is also available from the NCCB/CBS (The Netherlands Culture Collection of Bacteria) at the same address as that indicated above.

3. Plasmids pCL1920 and pCL1921 were obtained from Dr. M. Inouye, Dept. of Biochemistry, UMDNJ-Robert Wood Johnson Medical School, Piscataway, 08854-5635, USA, and are described in Lerner and Inouye [Nucleic Acids Res. (1990) 15:4631]; these two plasmids are also available from the NCCB/CBS (The Netherlands Culture Collection of Bacteria) at the same address as that indicated above. Plasmid pAM34 was obtained from Dr. J. P. Bouche, Centre de Recherche de Biochimie et de Genetique Cellulaires, CNRS, 31062 Toulouse, France, and is described in Gil and Bouche [Gene (1991) 105:17–22]; it is also available in the American Type Culture Collection (ATCC), P.O. Box 1549, Manassas, Va. 20108, USA. Plasmid pMAK705 was obtained from Dr. S. R. Kushner, Dept. of Genetics, University of Georgia, Athens, Ga. 30602, USA, and is described in Hamilton et al. [J. Bacteriol. (1989) 171:4617–4622]. Plasmid pUC4K was obtained from Dr. S. R. Kushner at the same address as that indicated above, and it is also available from Amersham Biosciences Inc., 800 Centennial Avenue, P.O. Box 1327, Piscataway, N.J. 08855-1327, U.S.A. Plasmids pACYC184, pBR329, and pUC19 are described in, respectively, Chang and Cohen (1978) J. Bacteriol. 134:1141–1156, Covarrubias and Bolivar (1982) Gene 17:79–89, and Yanisch-Perron et al. (1985) Gene 33:103–119; all these three plasmids are available from both the American Type Culture Collection (ATCC) and the NCCB/CBS at their respective addresses indicated above; plasmids pACYC184 and pUC19 are also available from New England Biolabs Inc., 32 Tozer Road, Beverly, Mass. 01915-5599, U.S.A. Plasmid pBluescript II-KS was obtained from Stratagene Inc., 11011 N. Torrey Pines Road, La Jolla, Calif. 92037, U.S.A. Plasmid pPMrhoCam was obtained from Dr. J. P. Richardson, Dept. of Chemistry, Indiana University, Bloomington, 47405, USA, and is described in Martinez et al. [J. Mol. Biol. (1996) 257:895–908].

3. Bacteriological media materials were purchased from Difco Laboratories (P.O. Box 331058, Detroit, Mich. 48232-7058, USA). Antibiotics and fine chemicals were purchased from Sigma (P.O. Box 14508, St. Louis, Mo. 63178, USA). Restriction endonucleases and enzymes used during DNA cloning were obtained from New England Biolabs (32 Tozer Rd, Beverly, Mass. 01915-5599, USA).

4. Nutrient and glucose-minimal growth media were derived, respectively, from LB and minimal A media described in "A Short Course in Bacterial Genetics: A Laboratory Manual and Handbook for *Escherichia coli* and Related Bacteria" by J. H. Miller (1992), Cold Spring Harbor Laboratory Press, Cold Spring Harbor, N.Y., USA. When needed, supplementation of minimal growth medium with particular amino acids to satisfy an auxotrophic requirement was at a final concentration of 40 micrograms/ml each. Antibiotics were used (when needed) at the following final concentrations (micrograms/ml): ampicillin (Amp), 100; tetracycline (Tet), 15; chloramphenicol (Cm), 30; kanamycin (Kan), 50; and spectinomycin (Sp), 50. Superscripts r and s are used to denote the phenotypes of resistance and sensitivity respectively. Stock solutions of Amp, Kan, and Sp were prepared in water and those of Tet and Cm in ethanol. IPTG was prepared as a stock solution of 100 mM in water and used at a final concentration of 1 mM.

5. Procedures for P1 transduction, and for most other routine microbial genetic techniques were as described in the reference of Miller cited above. Strains were classified as SMG-resistant (or SMG-sensitive) based on their ability (or inability) to grow at 37° C. on glucose-minimal A agar plates supplemented with 0.05 mg/ml each of L-serine, L-methionine, and glycine (plus other auxotrophic requirements as appropriate and indicated). Unless mentioned otherwise, the procedures for preparation of plasmid and lambda phage DNAs, the preparation and cloning of DNA fragments, and plasmid transformations, were by the standard techniques described in "Molecular Cloning: A Laboratory Manual, Second Edition" by Sambrook et al. (1989), Cold Spring Harbor Laboratory Press, Cold Spring Harbor Laboratory, N.Y., USA. Unless otherwise indicated, strain derivatives carrying the IPTG-dependent conditional replicon plasmid pAM34 or its derivatives were grown in medium supplemented with Amp and IPTG. Unless otherwise indicated, strain derivatives carrying the temperature-sensitive conditional replicon plasmid pMAK705 or its derivatives were grown at a temperature of 30° C.

6. Data on the DNA sequence and physical map of the *E. coli* genome were obtained from, respectively, Blattner et al. [Science (1997) 277:1453–1462] and Rudd [Microbiol. Mol. Biol. Rev. (1998) 62:985–1019]. Accession numbers in the GenBank sequence database (URL site address http://www.ncbi.nlm.nih.gov/Genbank) for the entire *E.coli* genome and for the segments carrying nusG and rho are, respectively, NC_000913, AE000472, and AE000454.

The present invention is described herein below with reference to examples, which are illustrative only and should not be construed to limit the scope of the present invention in any manner.

Example 1

Comparison of Plasmid pACYC184 Yields from Cultures of nusG+ Strain MC4100 and Isogenic nusG Mutant GJ1504

Strain GJ3158 is a strain of this invention which has been deposited under the accession number NCIMB 41132 at the NCIMB Ltd., Scotland, under the Budapest Treaty Rules. Strain GJ3158 carries a GC-to-AT transition mutation in codon 146 of the chromosomal nusG gene resulting in a glycine-to-aspartate substitution at the cognate amino acid position of the encoded protein, along with an argE86::Tn10 mutation approximately 25% linked to nusG in phage P1 transduction. A P1 lysate prepared on strain GJ3158 was used to transduce strain MC4100 to Tet$^r$ on LB-Tet agar plates at 37° C. Tet$^r$ transductants that had co-inherited the nusG mutation were identified based on the fact that they were SMG-resistant whereas nusG+ transductants were SMG-sensitive; this test was done on plates supplemented with L-arginine (to satisfy an auxotrophic requirement). One of the Tet$^r$ SMG-resistant transductants was then used as a recipient in transduction with a P1 lysate prepared on strain MC4100, and Arg$^+$ transductants that were selected were then screened for Tet$^s$ and SMG-resistance. One of the Arg$^+$ Tet$^s$ SMG-resistant transductants was saved and was designated GJ1504. Strain GJ1504 is therefore an isogenic nusG mutant derivative of strain MC4100.

Strains MC4100 and GJ1504 were transformed with plasmid pACYC184, and transformant colonies were selected by incubation for 14 hours at 30° C. on LB agar plates supplemented with Cm. A single colony each of MC4100/pACYC184 and GJ1504/pACYC184 was picked from the transformation plates, inoculated separately into 30 ml of LB medium supplemented with Cm in a 150-ml Erlenmeyer flask, and incubated in a gyrotary water bath shaker at 30° C. 3-ml aliquots from the cultures were taken at 2-hourly intervals beginning from 6 hours of inoculation until 18 hours. For each aliquot, the absorbance at 600 nm ($A_{600}$) was measured and plasmid preparation was made from a 2.5-ml volume. It was observed that for any given value of $A_{600}$ of the two cultures, the yield of pACYC184 DNA from GJ1504/pACYC184 was higher than that from MC4100/pACYC184, and that this difference was very substantial (around 10-fold or higher) at $A_{600}$ values of approximately 1.0 to 1.2. It was also observed that the predominant species of plasmid pACYC184 under these conditions in the derivative GJ1504/pACYC184 was of the form designated in the art as "covalently closed circular supercoiled monomers".

The substantial increase in plasmid content in pACYC184 transformants of strain GJ1504 was correlated with a sharp drop in viability of the said colonies and cultures after 24 to 36 hours' incubation at 30° C. We also obtained evidence that the activity of the enzyme chloramphenicol acetyl transferase, encoded by a gene on the plasmid pACYC184, was substantially elevated in the said cultures.

Transformant derivatives of GJ1504, but not of MC4100, with either of two other plasmids pUC19 or pBluescript II-KS were also found to exhibit very poor viability after 24 hours' incubation at 30° C.

Example 2

Construction of Temperature-sensitive Conditional Replicon Plasmid pHYD763 Carrying nusG$^+$ Gene and Demonstration of Increase in Plasmid pACYC184 Copy Number in GJ1504/pHYD763/pACYC184 After Temperature-Upshift from 30° C. to 43° C.

The rpoB2 (Ts) strain JBK246 was transduced to Kan$^r$ with a P1 lysate prepared on MC4100 recA::Kan, and the resulting JBK246 recA::Kan transductant was designated GJ1514.

Chromosomal DNA isolated from strain MC4100 was digested with BamHI and ligated with BamHI-digested plasmid vector pCL1920 DNA. The ligation mix was used to transform GJ1514 to Spec$^r$ at 42° C. Transformant colonies so obtained were expected to have a plasmid with a 22-kb BamHI fragment bearing the rpoB$^+$ gene from the MC4100 chromosome cloned into vector pCL1920, so as to complement the rpoB (Ts) mutation in GJ1514 for growth at 42° C. One plasmid with the desired insert so identified was designated pHYD541.

Plasmid pHYD541 was digested with HindIII and BamHI, and a 7.8-kb fragment expected to carry the nusG$^+$ gene was purified by elution from an agarose gel piece following agarose gel electrophoresis. The 7.8-kb fragment was cloned into the HindIII and BamHI sites of pCL1920 to generate plasmid pHYD545. Plasmid pHYD545 was in turn digested with SmaI, and a 3.8-kb fragment expected to carry the nusG$^+$ gene was purified by elution from an agarose gel piece following agarose gel electrophoresis. The 3.8-kb fragment was cloned into the SmaI site of pCL1920 to generate plasmid pHYD547. From pHYD547, a 3.8-kb BamHI-SacI fragment carrying nusG$^+$ was subsequently subcloned into the BamHI-SacI sites of the Cm$^r$ plasmid pMAK705, to generate plasmid pHYD763.

Strains MC4100 and GJ1504 were each successively transformed with plasmids pHYD763 and pACYC184, with selections for Cm$^r$ for pHYD763 and Tet$^r$ for pACYC184 transformations respectively. A single transformant colony each of GJ1504/pHYD763/pACYC184 and MC4100/pHYD763/pACYC184 was inoculated into 2 ml of LB supplemented with Cm and Tet and the cultures were grown to stationary phase by overnight incubation at 30° C. A 100-microliter volume of a 1:100 dilution prepared from each of the cultures was then inoculated into 10 ml of LB medium supplemented with Tet in a 150-ml Erlenmeyer flask. Both flasks were incubated with shaking at 43° C. in a gyrotary water bath shaker until the $A_{600}$ values of the respective cultures reached approximately 1.3, following which plasmid preparations were made from a 2.5-ml volume of culture taken from each flask. It was observed that the yield of plasmid pACYC184 from the culture of the GJ1504 derivative was substantially higher than that from the culture of the MC4100 derivative. It was also observed that there was a substantial drop in viability of the GJ1504-derived culture, but not of the MC4100-derived culture, at the harvest time-point.

Example 3

Construction of IPTG-dependent Conditional Replicon Plasmid pHYD751 Carrying nusG$^+$ Gene and Demonstration of Increase in Plasmid pUC4K Copy Number in GJ1504/pHYD751/pUC4K After IPTG-withdrawal Starting from plasmid pHYD547, a 2.1-kb EcoRI-SalI fragment carrying nusG$^+$ was subcloned into the EcoRI-SalI sites of the IPTG-dependent Amp$^r$ plasmid vector pAM34, to generate plasmid pHYD751.

Strains MC4100 and GJ1504 were each successively transformed with plasmids pHYD751 and pUC4K, with selections for Amp$^r$ (in the presence of IPTG) for pHYD751 and Kan$^r$ for pUC4K transformations respectively. A single transformant colony each of GJ1504/pHYD751/pUC4K and MC4100/pHYD751/pUC4K was inoculated into 2 ml of LB supplemented with Amp, Kan and IPTG and the cultures were grown to stationary phase by overnight incubation at 30° C. The cells in each culture were pelleted by centrifugation at 4000 rpm for 10 minutes in a bench-top centrifuge and then resuspended in 2 ml of fresh LB. A 10-microliter volume from each suspension was then inoculated into 10 ml of LB medium supplemented with Kan in a 150-ml Erlenmeyer flask. Both flasks were incubated with shaking at 30° C. in a gyrotary water bath shaker until the $A_{600}$ values of the respective cultures reached approximately 1.3, following which plasmid preparations were made from a 2.5-ml volume of culture taken from each flask. It was observed that the yield of plasmid pUC4K from the culture of the GJ1504 derivative was substantially higher than that from the culture of the MC4100 derivative. It was also observed that there was a substantial drop in viability of the GJ1504-derived culture, but not of the MC4100-derived culture, at the harvest time-point.

Example 4

Comparison of Plasmid pACYC184 Yields from Cultures of Isogenic rho⁺ Strain GJ862 and rho-4 Mutant GJ863

The isogenic rho strains GJ862 and GJ863 were constructed in two steps of P1 transduction as follows. In the first step, a P1 lysate prepared on strain CAG18431 was used to transduce MC4100 to Tet$^r$ Ilv$^-$. One such transductant was used as recipient in the second step for infection with a P1 lysate prepared on the rho-4 mutant strain CGSC5072, and Ilv⁺ transductants were selected (all of which had also become Tet$^s$). Approximately 20% of the Ilv⁺ Tet$^s$ transductants behaved like MC4100 in that they were SMG-sensitive, whereas the remaining 80% had become SMG-resistant and were presumed to have inherited the linked rho-4 allele. One SMG-sensitive and one SMG-resistant transductant from the second cross were used in further work and were designated GJ862 and GJ863, respectively. DNA sequence determination of the chromosomal rho gene in GJ863 indicated that the rho-4 mutation is a GC-to-TA transversion mutation in codon 243 resulting in an alanine-to-glutamate substitution at the cognate amino acid position of the encoded protein.

Strains GJ862 and GJ863 were transformed with plasmid pACYC184, and transformant colonies were selected by incubation for 14 hours at 30° C. on LB agar plates supplemented with Cm. A single colony each of GJ862/pACYC184 and GJ863/pACYC184 was picked from the transformation plates, inoculated separately into 30 ml of LB medium supplemented with Cm in a 150-ml Erlenmeyer flask, and incubated in a gyratory water bath shaker at 30° C. 3-ml aliquots from the cultures were taken at 2-hourly intervals beginning from 6 hours of inoculation until 18 hours. For each aliquot, the ($A_{600}$) was measured and plasmid preparation was made from a 2.5 ml volume. It was observed that for any given value of $A_{600}$ of the two cultures, the yield of pACYC184 DNA from GJ863/pACYC184 was higher than that from GJ862/pACYC184, and that this difference was very substantial (around 10-fold or higher) at $A_{600}$ values of approximately 1.0 to 1.2.

The substantial increase in plasmid content in pACYC184 transformants of strain GJ863 was also correlated with a sharp drop in viability of the said colonies and cultures after 24 to 36 hours' incubation at 30° C.

Transformant derivatives of GJ863, but not of GJ862, with either of two other plasmids pUC19 or pBluescript II-KS were also found to exhibit very poor viability after 24 hours' incubation at 30° C.

Example 5

Use of Temperature-sensitive Conditional Replicon Plasmid pPMrhoCam Carrying rho⁺ Gene to Demonstrate Increase in Plasmid pACYC184 Copy Number in GJ863/pPMrhoCam/pACYC184 After Temperature-upshift from 30° C. to 43° C.

Strains MC4100 and GJ863 were each successively transformed with plasmids pPMrhoCam (a temperature-sensitive conditional replicon carrying the rho⁺ gene) and pACYC184, with selections for Cm$^r$ for pPMrhoCam and Tet$^r$ for pACYC184 transformations respectively. A single transformant colony each of GJ863/pPMrhoCam/pACYC184 and MC4100/pPMrhoCam/pACYC184 was inoculated into 2 ml of LB supplemented with Cm and Tet and the cultures were grown to stationary phase by overnight incubation at 30° C. A 100-microliter volume of a 1:100 dilution prepared from each of the cultures was then inoculated into 10 ml of LB medium supplemented with Tet in a 150-ml Erlenmeyer flask. Both flasks were incubated with shaking at 43° C. in a gyratory water bath shaker until the $A_{600}$ values of the respective cultures reached approximately 1.3, following which plasmid preparations were made from a 2.5-ml volume of culture taken from each flask. It was observed that the yield of plasmid pACYC184 from the culture of the GJ863 derivative was substantially higher than that from the culture of the MC4100 derivative. It was also observed that there was a substantial drop in viability of the GJ863-derived culture, but not of the MC4100-derived culture, at the harvest time-point.

Example 6

Construction of IPTG-dependent Conditional Replicon Plasmid pHYD1201 Carrying rho⁺ Gene and Demonstration of Increase in Plasmid pUC4K Copy Number in GJ863/pHYD1201/pUC4K After IPTG-withdrawal The IPTG-dependent conditional replicon plasmid pHYD1201 was constructed in three steps as follows. Starting from DNA of lambda phage clone 556 from the ordered lambda phage library of the *E. coli* genome described by Kohara et al. [Cell (1987) 50:495–508], a 6.7-kb HindIII fragment carrying the rho⁺ gene was subcloned into the HindIII site of plasmid vector pCL1921, and one plasmid so obtained was designated pHYD552. In the second step, a 3.3-kb NsiI fragment from pHYD552 carrying the rho⁺ gene was cloned into the PstI site of plasmid vector pCL1920 to obtain the plasmids pHYD567 and pHYD568 (representing the two orientations of the insert with respect to the vector). The insert DNA in pHYD567 is flanked by (among others) a SalI site on one side (proximal to rho⁺ promoter) and a HindIII site on the other. In the third step, the HindIII-SalI fragment from pHYD567 (carrying rho⁺) was cloned into the HindIII-SalI sites of plasmid vector pAM34, in order to generate plasmid pHYD1201. Amp$^r$ transformants in the third step were selected on plates supplemented with IPTG.

Strains GJ862 (rho⁺) and GJ863 (rho-4) were each successively transformed with plasmids pHYD1201 and pUC4K, with selections for Amp$^r$ (in the presence of IPTG) for pHYD1201 and Kan$^r$ for pUC4K transformations respectively. A single transformant colony each of GJ862/pHYD1201/pUC4K and GJ863/pHYD1201/pUC4K was inoculated into 2 ml of LB supplemented with Amp, Kan and IPTG and the cultures were grown to stationary phase by overnight incubation at 30° C. The cells in each culture were pelleted by centrifugation at 4000 rpm for 10 minutes in a bench-top centrifuge and then resuspended in 2 ml of fresh LB. A 10-microliter volume from each suspension was then inoculated into 10 ml of LB medium supplemented with Kan in a 150-ml Erlenmeyer flask. Both flasks were incubated with shaking at 30° C. in a gyratory water bath shaker until the $A_{600}$ values of the respective cultures reached approximately 1.3, following which plasmid preparations were made from a 2.5-ml volume of culture taken from each flask. It was observed that the yield of plasmid pUC4K from the culture of the GJ863 derivative was substantially higher than that from the culture of the GJ862 derivative. It was also observed that there was a substantial drop in viability of the GJ863-derived culture, but not of the GJ862-derived culture, at the harvest time-point.

Example 7

Comparison of Yields of Plasmids pACYC184, pBR329, and pUC19 from Cultures of derivatives of dnaC⁺ strain GJ3141 and isogenic dnaC mutant GJ3140

Strain GJ3158 is a strain of this invention which has been deposited under the accession number NCIMB 41132 at the NCIMB Ltd., Scotland, under the Budapest Treaty Rules. Strain GJ3158 carries a GC-to-AT transition mutation in codon 84 of the chromosomal dnaC gene resulting in an alanine-to-threonine substitution at the cognate amino acid position of the encoded protein, along with an zjj-901::Tn10dKan insertion approximately 88% linked to dnaC in phage P1 transduction. A P1 lysate prepared on strain GJ3158 was used to transduce strain MC4100 to Kan$^r$ on LB Kan agar plates at 37° C. Kan$^r$ transductants that had co-inherited the dnaC mutation were identified based on the fact that when subsequently transformed to Amp$^r$ at 30° C. with plasmid pUC19, the transformant derivatives were also able to grow at 42° C. whereas those Kan$^r$ transductants that had retained the parental dnaC⁺allele yielded pUC19-Amp$^r$ transformant that failed to grow at 42° C. One each of the Kan$^r$ dnaC⁺and Kan$^r$ dnaC transductants so identified were designated as GJ3141 and GJ3140, respectively.

Strains GJ3141 and GJ3140 were each transformed with plasmids pACYC184, pBR329, or pUC19 with selections at 30° C. for Cm$^r$, Amp$^r$, or Amp$^r$ colonies respectively. The transformant derivatives were grown at 30° C. in LB supplemented with the appropriate antibiotics to an $A_{600}$ value of approximately 1.6, and plasmid preparations were made from 2.5-ml volumes of each culture. It was observed that the yields of each of the three plasmids was substantially lower from the GJ3140 derivatives than that from the corresponding GJ3141 derivatives.

Two lines of evidence were obtained to indicate that the dnaC mutation acts independently of the nusG and rho mutations in altering plasmid content in host bacterial cells, thus enabling the artisan to employ various mutational combinations (of nusG or rho on the one hand, and dnaC on the other) to modulate plasmid yields from the said cells: (i) When the dnaC mutation was introduced (by phage P1-mediated transduction) from strain GJ3158 into either the nusG strain GJ1504 or the rho strain GJ863 and plasmid pACYC184 was subsequently transformed into the resulting derivatives, plasmid yield from the said transformants was higher than that from GJ3140/pACYC184 but lower than from either GJ1504/pACYC184 or GJ863/pACYC184. (ii) Whereas pACYC184 transformants of GJ1504 and GJ863 exhibited a sharp drop in viability after 24 to 36 hours' incubation at 30° C., similar transformants of the dnaC mutant derivatives of GJ1504 and GJ863 did not exhibit any loss of viability. Very similar results were also obtained when plasmid pUC19 transformants of the various strains were tested.

REFERENCES CITED

Polisky (1988) Cell 55:929–932
Lin-Chao et al. (1992) Mol. Microbiol. 6:3385–3393
Nordstrom and Uhlin (1992) Bio/Technology 10:661–666
Lopilato et al. (1986) Mol. Gen. Genet. 205:285–290
Sullivan et al. (1992) Cell 68:989–994
Martinez et. al. (1996) J. Mol. Biol. 257:895–908
Marians (1996) "Replication Fork Progression", in *Escherichia coli* and *Salmonella*: Cellular and Molecular Biology, 2$^{nd}$ edition" (Neidhardt et al., eds), ASM Press, Washington D.C., USA, Chapter 50, pp. 749–763
Kohara et al. (1987) Cell 50:495–508
Lemer and Inouye (1990) Nucleic Acids Res. 18:4631
Gil and Bouche (1991) Gene 105:17–22
Hamilton et al. (1989) J. Bacteriol. 171:4617–4622
Chang and Cohen (1978) J. Bacteriol. 134:1141–1156
Covarrubias and Bolivar (1982) Gene 17:79–89
Yanisch-Perron et al. (1985) Gene 33:103–119
Miller (1992) "A Short Course in Bacterial Genetics: A Laboratory Manual and Handbook for *Escherichia coli* and Related Bacteria", CSH Press, Cold Spring Harbor Laboratory, New York, USA
Sambrook et al. (1989) "Molecular Cloning: A Laboratory Manual, 2$^{nd}$ Edition", CSH Press, Cold Spring Harbor Laboratory, New York, USA
Blattner et al. (1997) Science 277:1453–1462
Rudd (1998) Microbiol. Mol. Biol. Rev. 62:985–1019

We claim:

1. A method of obtaining increased plasmid content in bacteria, said method comprising steps of:
   a) introducing the plasmid into said bacteria;
   b) introducing a mutation in chromosomal gene nusG of the bacteria;
   c) maintaining a functional copy of said chromosomal gene on a conditional replicon in said bacteria;
   d) culturing said bacteria under a condition permissive for intracellular replication and maintenance of said conditional replicon;
   e) culturing the bacterial under a restrictive condition that does not permit further intracellular replication of the conditional replicon;
   f) estimating the level of said plasmid in the bacteria cultured under both permissive and restrictive conditions, and
   g) comparing the level of said plasmid in the bacteria cultured under permissive and restrictive conditions,
   wherein a difference in the level of plasmid from bacteria cultured under permissive conditions and the level of plasmid from bacteria cultured under restrictive conditions is an indication of increased plasmid content,
   wherein the mutation in gene nusG is a GC-to-AT transition mutation at codon 146 of the gene, and the bacteria are *Escherichia coli*.

2. The method as claimed in claim 1, wherein the mutation results in a protein with a glycine-to-aspartate substitution at the corresponding amino acid position.

3. The method of claim 1, wherein the plasmid is selected from the group consisting of plasmids bearing the ColE1 origin of replication and plasmids bearing the p15A origin of replication.

4. The method of claim 3, wherein the plasmids bearing the ColE1 origin of replication are members of an incompatibility group selected from the group consisting of pBR322, pBR329, pUC plasmids, and pBluescript plasmids bearing the origins of replication of any of these plasmids.

5. The method of claim 1, wherein the increase is about 10 fold.

6. The method of claim 1, wherein the conditional replicon is selected from the group consisting of pHYD751 and pHYD763.

* * * * *